(12) United States Patent
Lizardi

(10) Patent No.: US 6,642,034 B2
(45) Date of Patent: *Nov. 4, 2003

(54) MULTIPLE DISPLACEMENT AMPLIFICATION

(75) Inventor: Paul M. Lizardi, Hamden, CT (US)

(73) Assignee: Yale University, New Haven, CT (US)

( * ) Notice: Subject to any disclaimer, the term of this patent is extended or adjusted under 35 U.S.C. 154(b) by 80 days.

This patent is subject to a terminal disclaimer.

(21) Appl. No.: 09/911,226

(22) Filed: Jul. 23, 2001

(65) Prior Publication Data

US 2003/0143536 A1 Jul. 31, 2003

Related U.S. Application Data

(63) Continuation of application No. 09/397,915, filed on Sep. 17, 1999, now Pat. No. 6,280,949, which is a continuation of application No. 08/946,732, filed on Oct. 8, 1997, now Pat. No. 6,124,120.

(51) Int. Cl.$^7$ ................................................. C12P 19/34
(52) U.S. Cl. ..................... 435/91.1; 435/6; 435/91.2; 435/91.52; 435/91.51; 536/24.3
(58) Field of Search ..................... 435/6, 91.2, 91.52, 435/91.51, 91.1; 536/24.3

(56) References Cited

U.S. PATENT DOCUMENTS

| 4,994,373 A | | 2/1991 | Stavrianopoulos et al. |
| 5,001,050 A | | 3/1991 | Blanco et al. |
| 5,043,272 A | * | 8/1991 | Hartley ........................ 435/91 |

(List continued on next page.)

FOREIGN PATENT DOCUMENTS

| EP | 0 128 332 A2 | 12/1984 |
| EP | 0 466 520 | 1/1992 |
| EP | 0 667 393 A2 | 8/1995 |
| WO | WO 95/03430 | 2/1995 |
| WO | WO 95/25180 | 9/1995 |
| WO | WO 97/19193 | 5/1997 |

OTHER PUBLICATIONS

Walker et al., Nucleic acid research, 1992, vol. 20(7), p. 1691–1696.*
Jiang et al., Nucleic acid research, 1996, vol. 24(6), p. 3278–3279.*

(List continued on next page.)

*Primary Examiner*—Ethan Whisenant
*Assistant Examiner*—Joyce Tung
(74) *Attorney, Agent, or Firm*—Needle & Rosenberg, P.C.

(57) ABSTRACT

Disclosed are compositions and a method for amplification of nucleic acid sequences of interest. The method is based on stand displacement replication of the nucleic acid sequences of interest by multiple primers. In one preferred form of the method, referred to as multiple strand displacement amplification, two sets of primers are used, a right set and a left set. The primers in the right set are complementary to one strand of the nucleic acid molecule to be amplified and the primers in the left set are complementary to the opposite strand. The 5' end of primers in both sets are distal to the nucleic acid sequence of interest when the primers have hybridized to the nucleic acid sequence molecule to be amplified. Amplification proceeds by replication initiated at each primer and continuing through the nucleic acid sequence of interest. A key feature of this method is the displacement of intervening primers during replication by the polymerase. In another preferred form of the method, referred to as whole genome strand displacement amplification, a random set of primers is used to randomly prime a sample of genomic nucleic acid (or another sample of nucleic acid of high complexity). By choosing a set of primers which are sufficiently random, the primers in the set will be collectively, and randomly, complementary to nucleic acid sequences distributed throughout nucleic acid in the sample. Amplification proceeds by replication with a highly processive polymerase initiated at each primer and continuing until spontaneous termination. A key feature of this method is the displacement of intervening primers during replication by the polymerase. In this way, multiple overlapping copies of the entire genome to be synthesized in a short time.

42 Claims, 4 Drawing Sheets

U.S. PATENT DOCUMENTS

| | | | |
|---|---|---|---|
| 5,198,543 A | * 3/1993 | Blanco et al. | 536/23.2 |
| 5,328,824 A | 7/1994 | Ward et al. | |
| 5,547,843 A | 8/1996 | Studier et al. | |
| 5,614,390 A | * 3/1997 | McCaslin et al. | 435/91.2 |
| 5,629,179 A | * 5/1997 | Mierendorf et al. | 435/91.2 |
| 5,854,033 A | 12/1998 | Lizardi | |
| 6,124,120 A | * 9/2000 | Lizardi | 435/91.2 |
| 6,143,495 A | 11/2000 | Lizardi et al. | |
| 6,183,960 B1 | 2/2001 | Lizardi | |
| 6,210,884 B1 | 4/2001 | Lizardi | |
| 6,255,082 B1 | 7/2001 | Lizardi | |
| 6,280,949 B1 | * 8/2001 | Lizardi | 435/6 |
| 6,329,150 B1 | 12/2001 | Lizardi et al. | |
| 6,344,329 B1 | 2/2002 | Lizardi | |

OTHER PUBLICATIONS

Aliotta, et al., "Thermostable Bst DNA polymerase I lacks a 3' →5' proofreading exonuclease activity," *Genet. Anal. (Netherlands)* 12:185–195 (1996).

Arnold, et al., "Assay Formats Involving Acridinium–Ester–Labeled DNA Probes," *Clin. Chem.* 35(8):1588–1594 (1989).

Birkenmeyer, et al., "Mini–Review: DNA probe amplification methods," *J. Virological Methods* 35:117–126 (1991).

Boehmer, et al., "Herpes Simplex Virus Type 1 1CP8: Helix–Destabilizing Properties," *J. Virology* 67(2):711–715 (1993).

Brownstein, et al., "Modulation of Non–Templated Nucleotide Addition by Taq DNA Polymerase: Primer Modifications that Facilitate Genotyping," *Biotechniques* 20(6):1004–1010 (1996).

Chatterjee, et al., "Cloning and overexpression of the gene encoding bacteriophage T5 DNA polymerase," *Gene* 97(1):13–19 (1991).

Cheung, et al., "Whole genome amplification using degenerate oligonucleotide primer allows hundreds of genotypes to be performed on less than one nanogram of genomic DNA," *Proc. Natl. Acad. Sci. USA* 93(25):14676–14679 (1996).

Guo, et al., "Direct fluorescence analysis of genetic polymorphisms by hyridization with oligonucleotide arrays on glass supports," *Nucleic Acids Res.* 22(24):5456–5465 (1994).

Holton, et al., "A simple and efficient method for direct cloning of PCR products using ddT–tailed vectors," *Nucl. Acids Res.* 19(5):1156 (1991).

Hoy, et al., "Bromodeoxyuridine/DNA analysis of replication in CHO cells after exposure to UV light," *Mutation Research* 290(2):217–230 (1993).

Itakura, et al., "Synthesis and use of synthetic oligonucleotides," *Ann Rev. Biochem.* 53:323–356 (1984).

Jacobsen, et al., "The N–Terminal Amino–Acid Sequences of DNA Polymerase I from *Escherichia coli* and of the Large and Small Fragments Obtained by a Limited Proteolysis," *Eur. J. Biochem.* 45(2):623–627 (1974).

Jiang, et al., "An efficient method for generation and subcloning of tandemly repeated DNA sequences with defined length, orientation and spacing," *Nuc. Acids Res.* 24(16):3278–3279 (1996).

Jung, et al., "Bacteriophage PRD1 DNA polymerase: Evolution of DNA polymerases," *Proc. Natl. Acad. Sci. USA* 84(23):8287–8291 (1987).

Kaboord, et al., "Accessory proteins function as matchmakers in the assembly of the T4 DNA polymerase holoenzyme," *Curr. Biol.* 5(2):149–157 (1995).

Kerkhof, "A Comparison of Substrates for Quantifying the Signal from a Nonradiolabeled DNA Probe," *Anal. Biochem.* 205(2):359–364 (1992).

Khrapko, et al., "Hybridization of DNA with Oligonucleotides Immobilized in Gel: A Convenient Method for Detecting Single Base Substitutions," *Mol Biol (Mosk) (USSR)* 25(3):718–730 (translation pp. 581–591) (1991).

Kong, et al., "Characterization of a DNA Polymerase from the Hyperthermophile Archaea *Thermococcus litoralis*," *J. Biol. Chem.* 268(3):1965–1975 (1993).

Kuukasjärvi, et al., "Optimizing DOP–PCR for Universal Amplification of Small DNA Samples in Comparative Genomic Hybridization," *Genes, Chromosomes and Cancer* 18:94–101 (1997).

Landegren, "Molecular mechanics of nucleic acid sequence amplification," *Trends Genetics* 9(6):199–202 (1993).

Langer, et al., "Enzymatic synthesis of biotin–labeled polynucleotides: Novel nucleic acid affinity probes," *Proc. Natl. Acad. Sci. USA* 78(11):6633–6637 (1981).

Lesnick, et al., "Relative Thermodynamic Stability of DNA, RNA, and DNA:RNA Hybrid Duplexes: Relationship with Base Composition and Structure," *Biochemistry* 34:10807–10815 (1995).

Lockhart, et al., "Expression monitoring by hybridization to high–density oligonucleotide arrays," *Nature Biotechnology* 14(13):1675–1680 (1996).

Matsumoto, et al., "Primary structure of bacteriophage M2 DNA polymerase: conversed segments within protein–priming DNA polymerases and DNA polymerase I of *Escherichia coli* (Recombinant DNA; nucleotide sequence; amino acid sequence; protein homology; aphidicolin–resistance mutation; dNTP–bonding site)," *Gene* 84(2):247–255 (1989).

McGraw, et al., "Sequence–Dependent Oligonucleotide–Target Duplex Stabilities: Rules from Empirical Studies with a Set of Twenty–Mers," *Biotechniques* 8(6):674–678 (1990).

Narang, et al., "Chemical Synthesis of Deoxyoligonucleotides by the Modified Triester Method," *Methods in Enzymology* vol. 65, Chap. 61, pp. 610–620 (Grossman, ed.) (Academic Press, Inc., 1980).

Nielsen, et al., "Peptide Nucleic Acid (PNA). A DNA Mimic with a Peptide Backbone," *Bioconjug. Chem.* 5(1):3–7 (1994).

Parker, et al., "Targeted Gene Walking Polymerase Chain Reaction," *Nucleic Acids Research* 19(11): 3055–3060 (1991).

Pease, et al., "Light–generated oligonucleotide arrays for rapid DNA sequence analysis," *Proc. Natl. Acad. Sci. USA* 91(11):5022–5026 (1994).

Rigler, et al., "Differences in the Mechanism of Stimulation of T7 DNA Polymerase by Two Binding Modes in *Escherichia coli* Single–stranded DNA–binding Protein," *J. Biol. Chem.* 270(15):8910–8919 (1995).

Rychlik, et al., "Optimization of the annealing temperature for DNA amplification in vitro," *Nucleic Acids Res.* 18(21):6409–6412 (1990).

Schena, et al., "Quantitative Monitoring of Gene Expression Patterns with a Complementary DNA Microarray," *Science* 270:467–470 (1995).

Siegel, et al., "A Novel DNA Helicase from Calf Thymus," *J. Biol. Chem.* 267(19):13629–13635 (1992).

Skaliter, et al., "Rolling circle DNA replication in vitro by a complex of herpes simplex virus type 1–encoded emzymes," *Proc. Natl. Acad. Sci. USA* 91(22):10665–10669 (1994).

Stimpson, et al., "Real–time detection of DNA hybridization and melting on oligonucleotide arrays by using optical wave guides," *Proc. Natl. Acad. Sci. USA* 92(14):6379–6383 (1995).

Telenius, et al., "Degenerate Oligonucleotide–Primed PCR: General Amplification of Target DNA by a Single Degenerate Primer," *Genomics* 13(3):718–725 (1992).

Tsurumi, et al., "Functional Interaction between Epstein–Barr Virus DNA Polymerase Catalytic Subunit and Its Accessory Subunit In Vitro," *J. Virology* 67(12):7648–7653 (1993).

Tyagi, et al., "Molecular Beacons: Probes that Fluoresce upon Hybridization," *Nature Biotechnol.* 14(3):303–309 (1995).

Villemain, et al., "The N–Terminal B–Domain of T4 Gene 32 Protein Molecules the Lifetime of Cooperatively Bound Gp32–ss Nucleic Acid Complexes," *Biochemistry* 35:14395–14404 (1996).

Walker, et al., "Strand Displacement Amplification–an Isothermal, in vitro DNA amplification technique," *Nuc. Acids Res.* 20(7):1691–1696 (1992).

Walker, et al., "Detection of *Mycobacterium tuberculosis* DNA with thermophilic strand displacement amplification and fluorescence polarization," *Clinical Chemistry* 42:1604–1608 (1996).

Wansinck, et al., "Fluorescent Labeling of Nascent RNA Reveals Transcription by RNA Polymerase II in Domains Scattered Throughout the Nucleus," *J. Cell Biology* 122:283–293 (1993).

Yu, et al., "Cyanine dye dUTP analogs for enzymatic labeling of DNA probes," *Nucleic Acids Res.*, 22(15):3226–3232 (1994).

Zhang, et al., "Whole genome amplification from a single cell: Implications for genetic analysis," *Proc. Natl. Acad. Sci. USA* 89(13):5847–5851 (1992).

Zhu, et al., "Purification and characterization of PRD1 DNA polymerase," *Biochim. Biophys. Acta* 1219(2):267–276 (1994).

Zijderveld, et al., "Helix–Destabilizing Properties of the Adenovirus DNA–Binding Protein," *J. Virology* 68(2):1158–1164 (1994).

\* cited by examiner

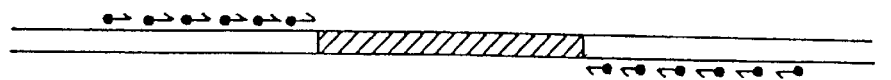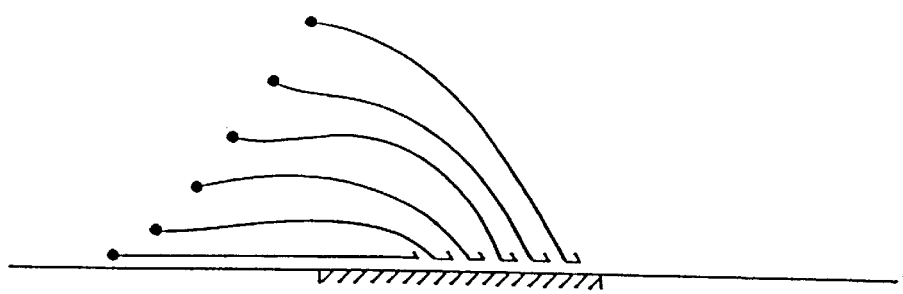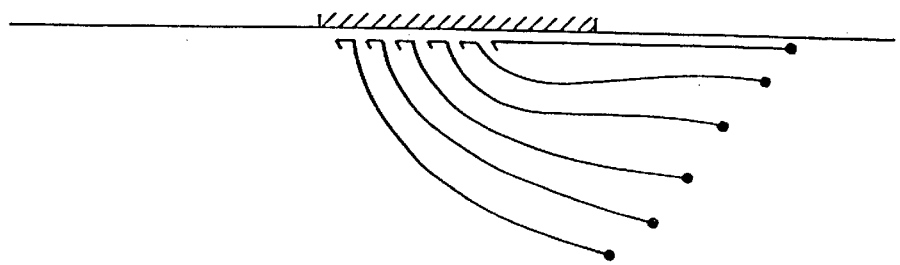
FIG. 1
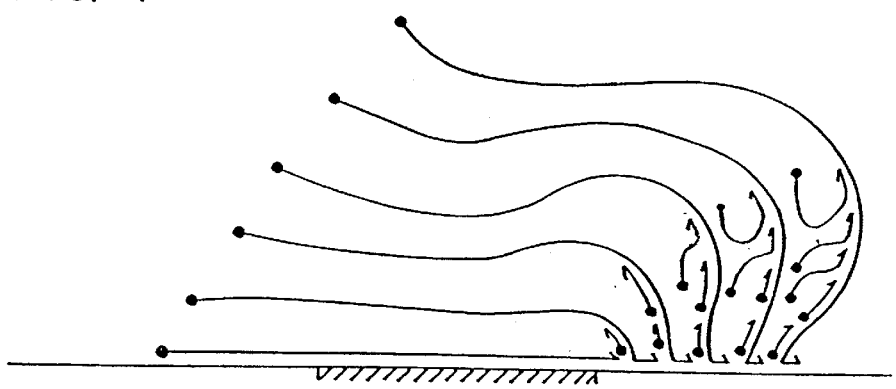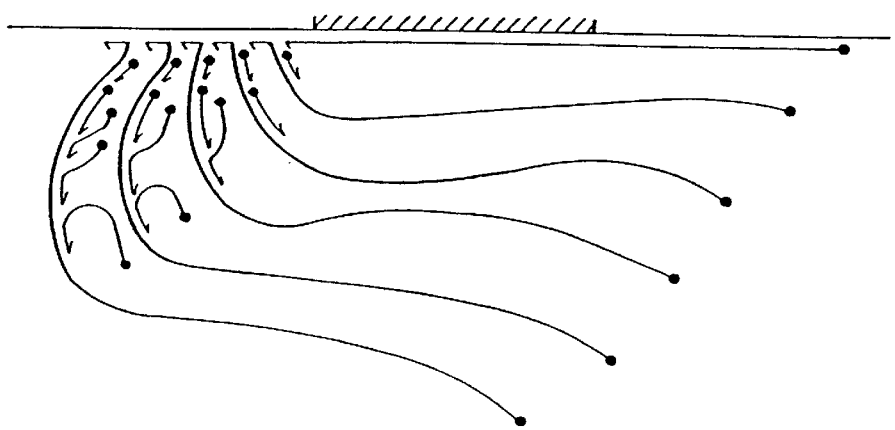

LINKER    LINKER    LINKER    LINKER

CONCATENATED DOUBLE-STRANDED DNA WITH MULTIPLE LINKERS

DENATURED DNA INCUBATED WITH TWO PRIMERS

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 1:

GTTGATACAT CAACTGCAC                  19

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 2:

CAATTACCTG AAGTCTTTC                  19

(2) INFORMATION FOR SEQ ID NO: 3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 3:

TTGTCATATT GTATCATGC                  19

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 4:

AAGATGAAAT AAGAGTAGC                                     19

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 5:

TGCATGCTAG ATGCTGATA                                     19

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 6:

TATGACTGTA CGCCACTGT                                     19

(2) INFORMATION FOR SEQ ID NO: 7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 7:

AGAGTTTCTT TGAGTAATC                                     19

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 8:

TTACAACCAC TAAACCCAC                                                19

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 9:

AATCGCCAGA GAAATCTAC                                                19

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 10:

AGGGTTATGC GTTGTTCCA                                                19

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 11:

TGTTAAGCAA CGCACTCTC                                                19

(2) INFORMATION FOR SEQ ID NO: 12:

(i) SEQUENCE CHARACTERISTICS:
        (A) LENGTH: 19 base pairs

```
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 12:

AGTCTGGCGT AACCATCAT                                                     19

(2) INFORMATION FOR SEQ ID NO: 13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 13:

AATAGTGTCT TTTGTGTCC                                                     19

(2) INFORMATION FOR SEQ ID NO: 14:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO: 14:

GCTTGTTACG GTTGATTTC                                                     19
```

MULTIPLE DISPLACEMENT AMPLIFICATION

MULTIPLE DISPLACEMENT AMPLIFICATION

This application is a continuation of application Ser. No. 09/397,915, filed Sep. 17, 1999, entitled "Multiple Displacement Amplification," by Paul M. Lizardi, now U.S. Pat. No. 6,280,949, which is a continuation of application Ser. No. 08/946,732, filed October 8, 1997, entitled "Multiple Displacement Amplification," by Paul M. Lizardi, now U.S. Pat. No. 6,124,120. Application Ser. No. 09/397,915, filed Sep. 17, 1999, and application Ser. No. 08/946,732, filed October 8, 1997, are hereby incorporated herein by reference.

BACKGROUND OF THE INVENTION

The disclosed invention is generally in the field of nucleic acid amplification.

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics* 9:199–202 (1993)).

Current methods of PCR amplification involve the use of two primers which hybridize to the regions flanking a nucleic acid sequence of interest such that DNA replication initiated at the primers will replicate the nucleic acid sequence of interest. By separating the replicated strands from the template strand with a denaturation step, another round of replication using the same primers can lead to geometric amplification of the nucleic acid sequence of interest. PCR amplification has the disadvantage that the amplification reaction cannot proceed continuously and must be carried out by subjecting the nucleic acid sample to multiple cycles in a series of reaction conditions.

A variant of PCR amplification, termed whole genome PCR, involves the use of random or partially random primers to amplify the entire genome of an organism in the same PCR reaction. This technique relies on having a sufficient number of primers of random or partially random sequence such that pairs of primers will hybridize throughout the genomic DNA at moderate intervals. Replication initiated at the primers can then result in replicated strands overlapping sites where another primer can hybridize. By subjecting the genomic sample to multiple amplification cycles, the genomic sequences will be amplified. Whole genome PCR has the same disadvantages as other forms of PCR.

Another field in which amplification is relevant is RNA expression profiling, where the objective is to determine the relative concentration of many different molecular species of RNA in a biological sample. Some of the RNAs of interest are present in relatively low concentrations, and it is desirable to amplify them prior to analysis. It is not possible to use the polymerase chain reaction to amplify them because the mRNA mixture is complex, typically consisting of 5,000 to 20,000 different molecular species. The polymerase chain reaction has the disadvantage that different molecular species will be amplified at different rates, distorting the relative concentrations of mRNAs.

Some procedures have been described that permit moderate amplification of all RNAs in a sample simultaneously. For example, in Lockhart et al., *Nature Biotechnology* 14:1675–1680 (1996), double-stranded cDNA was synthesized in such a manner that a strong RNA polymerase promoter was incorporated at the end of each cDNA. This promoter sequence was then used to transcribe the cDNAs, generating approximately 100 to 150 RNA copies for each cDNA molecule. This weak amplification system allowed RNA profiling of biological samples that contained a minimum of 100,000 cells. However, there is a need for a more powerful amplification method that would permit the profiling analysis of samples containing a very small number of cells.

Accordingly, there is a need for amplification methods that are less complicated, are more reliable, and produce greater amplification in a shorter time.

It is therefore an object of the disclosed invention to provide a method of amplifying a target nucleic acid sequence in a continuous, isothermal reaction.

It is another object of the disclosed invention to provide a method of amplifying an entire genome or other highly complex nucleic acid sample in a continuous, isothermal reaction.

It is another object of the disclosed invention to provide a method of amplifying a target nucleic acid sequence where multiple copies of the target nucleic acid sequence are produced in a single amplification cycle.

It is another object of the disclosed invention to provide a method of amplifying a concatenated DNA in a continuous, isothermal reaction.

It is another object of the disclosed invention to provide a kit for amplifying a target nucleic acid sequence in a continuous, isothermal reaction.

It is another object of the disclosed invention to provide a kit for amplifying an entire genome or other highly complex nucleic acid sample in a continuous, isothermal reaction.

SUMMARY OF THE INVENTION

Disclosed are compositions and a method for amplification of nucleic acid sequences of interest. The method is based on strand displacement replication of the nucleic acid sequences by multiple primers. In one preferred form of the method, referred to as multiple strand displacement amplification (MSDA), two sets of primers are used, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The 5' end of primers in both sets are distal to the nucleic acid sequence of interest when the primers are hybridized to the flanking sequences in the nucleic acid molecule. Preferably, each member of each set has a portion complementary to a separate and non-overlapping nucleotide sequence flanking the target nucleotide sequence. Amplification proceeds by replication initiated at each primer and continuing through the target nucleic acid sequence. A key feature of this method is the displacement of intervening primers during replication. Once the nucleic acid strands elongated from the right set of primers reaches the region of the nucleic acid molecule to which the left set of primers hybridizes, and vice versa, another round of priming and replication will take place. This allows multiple copies of a nested set of the target nucleic acid sequence to be synthesized in a short period of time. By using a sufficient number of primers in the right and left sets, only a few rounds of replication are required to produce hundreds of thousands of copies of the nucleic acid sequence of interest. The disclosed method has advantages over the polymerase chain reaction since it can be carried out under isothermal conditions. No thermal cycling is needed because the polymerase at the head of an elongating strand (or a compatible strand-displacement protein) will displace, and thereby make available for hybridization, the strand ahead of it. Other advantages of multiple strand displacement amplification include the ability to amplify very long nucleic acid segments (on the order of 50 kilobases) and rapid amplification of shorter segments (10 kilobases or less). In multiple strand displacement amplification, single priming events at unintended sites will not lead to artifactual amplification at these sites (since amplification at the intended site will quickly outstrip the single strand replication at the unintended site).

In another preferred form of the method, referred to as whole genome strand displacement amplification (WGSDA), a random set of primers is used to randomly prime a sample of genomic nucleic acid (or another sample of nucleic acid of high complexity). By choosing a sufficiently large set of primers of random or partially random sequence, the primers in the set will be collectively, and randomly, complementary to nucleic acid sequences distributed throughout nucleic acid in the sample. Amplification proceeds by replication with a highly processive polymerase initiating at each primer and continuing until spontaneous termination. A key feature of this method is the displacement of intervening primers during replication by the polymerase. In this way, multiple overlapping copies of the entire genome can be synthesized in a short time. The method has advantages over the polymerase chain reaction since it can be carried out under isothermal conditions. Other advantages of whole genome strand displacement amplification include a higher level of amplification than whole genome PCR (up to five times higher), amplification is less sequence-dependent than PCR, and there are no re-annealing artifacts or gene shuffling artifacts as can occur with PCR (since there are no cycles of denaturation and re-annealing).

In another preferred form of the method, referred to as multiple strand displacement amplification of concatenated DNA (MSDA-CD), fragments of DNA are first concatenated together, preferably with linkers. The concatenated DNA is then amplified by strand displacement synthesis with appropriate primers. A random set of primers can be used to randomly prime synthesis of the DNA concatemers in a manner similar to whole genome amplification. As in whole genome amplification, by choosing a sufficiently large set of primers of random or partially random sequence, the primers in the set will be collectively, and randomly, complementary to nucleic acid sequences distributed throughout concatenated DNA. If linkers are used to concatenate the DNA fragments, primers complementary to linker sequences can be used to amplify the concatemers. Synthesis proceeds from the linkers, through a section of the concatenated DNA to the next linker, and continues beyond. As the linker regions are replicated, new priming sites for DNA synthesis are created. In this way, multiple overlapping copies of the entire concatenated DNA sample can be synthesized in a short time.

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed a method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the whole genome strand displacement method.

BRIEF DESCRIPTION OF THE DRAWINGS

FIG. 1 is a diagram of an example of multiple strand displacement amplification (MSDA). Diagramed at the top is a double stranded nucleic acid molecule which contains a nucleic acid of interest (hatched area). Hybridized to the nucleic acid molecule are a right and left set of primers. Diagramed in the middle are the multiple strands of replicated nucleic acid being elongated from each primer. The polymerase at the end of each elongating strand displaces the elongating strand of the primer ahead of it. Diagramed at the bottom are the multiple strands of replicated nucleic acid further elongated. Also shown are the next sets of primers which hybridize to their complementary sites on the newly replicated strands. The newly replicated strands are made available for hybridization to the primers through displacement by the polymerase elongating the following strand.

Hybridized to the nucleic acid molecule are a right set of primers (top strand in top panel) and a left set of primers (bottom strand in top panel). Diagramed in the middle are the multiple strands of replicated nucleic acid being elongated from each primer. Also shown are the next sets of primers which hybridize to their complementary sites on the newly replicated strands. The newly replicated strands are made available for hybridization to the primers through displacement by the polymerase elongating the following strand. The polymerase at the end of each elongating strand displaces the elongating strand of the primer ahead of it. Diagramed at the bottom are the multiple strands of replicated nucleic acid further elongated. For simplicity only four of the originally synthesized strands (two on the upper target sequence strand and two on the lower target sequence strand) are depicted in the bottom panel.

Figure 4:
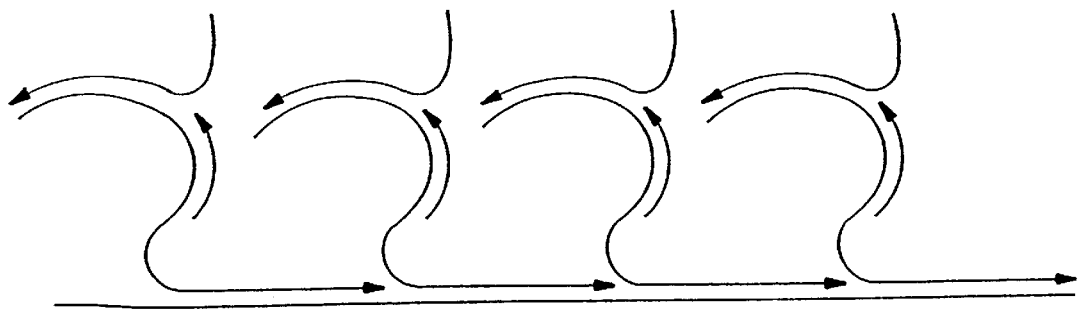
Figure 4:
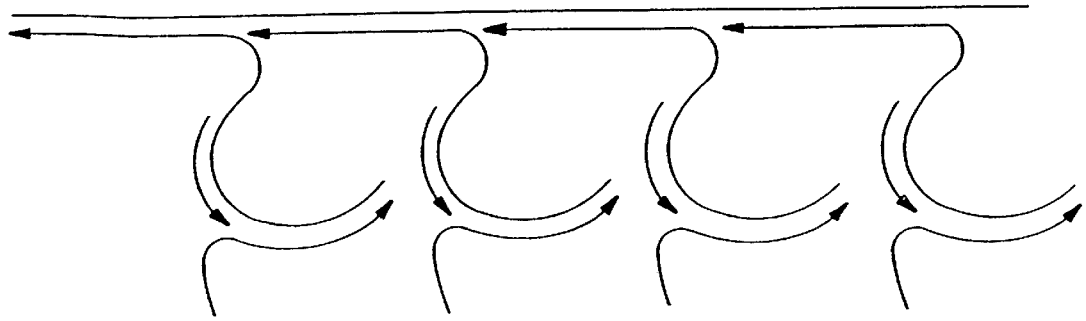

FIG. 4 is a diagram of an example of multiple strand displacement amplification of concatenated DNA (MSDA-CD). At the top is a diagrammatical representation of DNA concatenated with linkers. In the middle, primers complementary to linker sequences are hybridized to denatured strands of the concatenated DNA (the linker and primer lengths are not intended to be to scale). For simplicity, only a portion of one molecule of concatenated DNA is depicted. Diagramed at the bottom are the multiple strands of replicated nucleic acid being elongated from each primer. The polymerase at the end of each elongating strand displaces the elongating strand of any primer it encounters. Also shown are additional primers which hybridize to complementary sites in replicated linker sequences on the newly replicated strands. The newly replicated strands are made available for hybridization to the primers through displacement by the polymerase elongating a following strand.

DETAILED DESCRIPTION OF THE INVENTION

The disclosed method makes use of certain materials and procedures which allow amplification of target nucleic acid sequences and whole genomes or other highly complex nucleic acid samples. These materials and procedures are described in detail below.

I. MATERIALS

A. Target Sequence

The target sequence, which is the object of amplification, can be any nucleic acid. The target sequence can include multiple nucleic acid molecules, such as in the case of whole genome amplification, multiple sites in a nucleic acid molecule, or a single region of a nucleic acid molecule. For multiple strand displacement amplification, generally the target sequence is a single region in a nucleic acid molecule or nucleic acid sample. For whole genome amplification, the target sequence is the entire genome or nucleic acid sample. A target sequence can be in any nucleic acid sample of interest. The source, identity, and preparation of many such nucleic acid samples are known. It is preferred that nucleic acid samples known or identified for use in amplification or detection methods be used for the method described herein. The nucleic acid sample can be a nucleic acid sample from a single cell. For multiple strand displacement amplification, preferred target sequences are those which are difficult to amplify using PCR due to, for example, length or composition. For whole genome amplification, preferred target sequences are nucleic acid samples from a single cell. For multiple strand displacement amplification of concatenated DNA the target is the concatenated DNA. The target sequences for use in the disclosed method are preferably part of nucleic acid molecules or samples that are complex and non-repetitive (with the exception of the linkers in linker-concatenated DNA and sections of repetitive DNA in genomic DNA).

Figure 3:
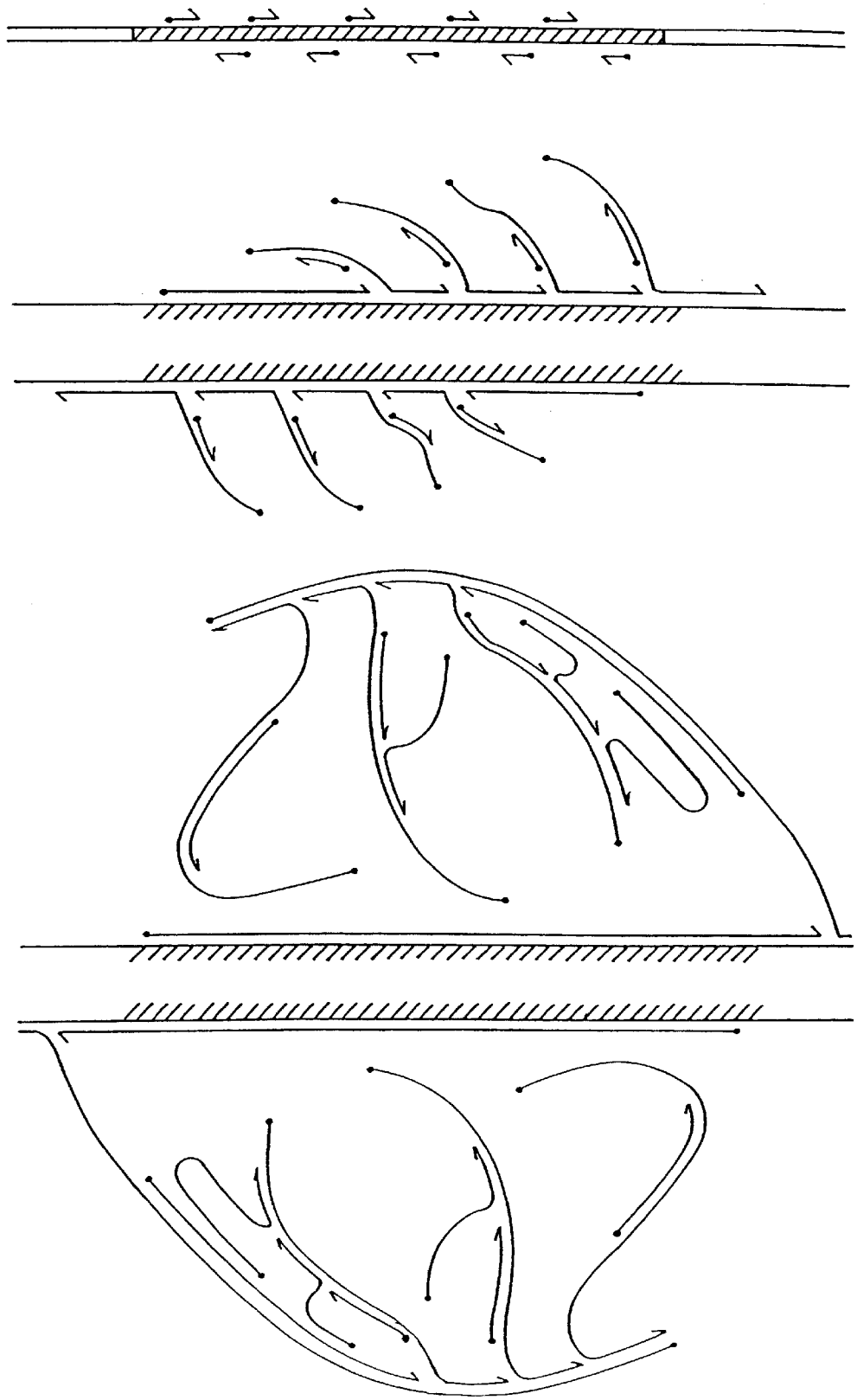
FIG. 3 is a diagram of an example of multiple strand displacement amplification (MSDA). Diagramed at the top is a double stranded nucleic acid molecule which contains a nucleic acid of interest (hatched area).

Target Sequences for Multiple Strand Displacement Amplification: Although multiple sites in a nucleic acid sample can be amplified simultaneously in the same MSDA reaction, for simplicity, the following discussion will refer to the features of a single nucleic acid sequence of interest which is to be amplified. This sequence is referred to below as a target sequence. It is preferred that a target sequence for MSDA include two types of target regions, an amplification target and a hybridization target. The hybridization target includes the sequences in the target sequence that are complementary to the primers in a set of primers. The amplification target is the portion of the target sequence which is to be amplified. For this purpose, the amplification target is preferably downstream of, or flanked by the hybridization target(s). There are no specific sequence or structural requirements for choosing a target sequence. The hybridization target and the amplification target within the target sequence are defined in terms of the relationship of the target sequence to the primers in a set of primers. The primers are designed to match the chosen target sequence. The top panel of FIG. 1 illustrates an example of how primers in a primer set can define the regions in a target sequence. Although preferred, it is not required that sequence to be amplified and the sites of hybridization of the primers be separate since sequences in and around the sites where the primers hybridize will be amplified. An example of this is illustrated in FIG. 3.

In multiple strand displacement amplification of linker-concatenated DNA, the DNA fragments joined by the linkers are the amplification targets and the linkers are the hybridization target. The hybridization targets (that is, the linkers) include the sequences that are complementary to the primers used for amplification. A preferred form of concatenated DNA for amplification is concatenated cDNA.

B. Primers

Primers for use in the disclosed amplification method are oligonucleotides having sequence complementary to the target sequence. This sequence is referred to as the complementary portion of the primer. The complementary portion of a primer can be any length that supports specific and stable hybridization between the primer and the target sequence. Generally this is 10 to 35 nucleotides long, but is preferably 16 to 24 nucleotides long. For whole genome amplification, it is preferred that the primers are from 12 to 60 nucleotides long.

It is preferred that primers also contain additional sequence at the 5' end of the primer that is not complementary to the target sequence. This sequence is referred to as the non-complementary portion of the primer. The non-complementary portion of the primer, if present, serves to facilitate strand displacement during DNA replication. The non-complementary portion of the primer can also include a functional sequence such as a promoter for an RNA polymerase. The non-complementary portion of a primer may be any length, but is generally 1 to 100 nucleotides long, and preferably 4 to 8 nucleotides long. The use of a non-complementary portion is not preferred when random or partially random primers are used for whole genome amplification.

Primers for Multiple Strand Displacement Amplification: In the case of multiple strand displacement amplification, the complementary portion of each primer is designed to be complementary to the hybridization target in the target sequence. In a set of primers, it is preferred that the complementary portion of each primer be complementary to a different portion of the target sequence. It is more preferred that the primers in the set be complementary to adjacent sites in the target sequence. It is also preferred that such adjacent sites in the target sequence are also adjacent to the amplification target in the target sequence.

It is preferred that, when hybridized to a target sequence, the primers in a set of primers are separated from each other.

It is preferred that, when hybridized, the primers in a set of primers are separated from each other by at least 5 bases. It is more preferred that, when hybridized, the primers in a set of primers are separated from each other by at least 10 bases. It is still more preferred that, when hybridized, the primers in a set of primers are separated from each other by at least 20 bases. It is still more preferred that, when hybridized, the primers in a set of primers are separated from each other by at least 30 bases. It is still more preferred that, when hybridized, the primers in a set of primers are separated from each other by at least 40 bases. It is still more preferred that, when hybridized, the primers in a set of primers are separated from each other by at least 50 bases.

It is preferred that, when hybridized, the primers in a set of primers are separated from each other by no more than about 500 bases. It is more preferred that, when hybridized, the primers in a set of primers are separated from each other by no more than about 400 bases. It is still more preferred that, when hybridized, the primers in a set of primers are separated from each other by no more than about 300 bases. It is still more preferred that, when hybridized, the primers in a set of primers are separated from each other by no more than about 200 bases. Any combination of the preferred upper and lower limits of separation described above are specifically contemplated, including all intermediate ranges. The primers in a set of primers need not, when hybridized, be separated from each other by the same number of bases. It is preferred that, when hybridized, the primers in a set of primers are separated from each other by about the same number of bases.

The optimal separation distance between primers will not be the same for all DNA polymerases, because this parameter is dependent on the net polymerization rate. A processive DNA polymerase will have a characteristic polymerization rate which may range from 5 to 300 nucleotides per second, and may be influenced by the presence or absence of accessory ssDNA binding proteins and helicases. In the case of a non-processive polymerase, the net polymerization rate will depend on the enzyme concentration, because at higher concentrations there are more re-initiation events and thus the net polymerization rate will be increased. An example of a processive polymerase is φ29 DNA polymerase, which proceeds at 50 nucleotides per second. An example of a non-processive polymerase is Vent exo(−) DNA polymerase, which will give effective polymerization rates of 4 nucleotides per second at low concentration, or 16 nucleotides per second at higher concentrations.

To obtain an optimal yield in an MSDA reaction, the primer spacing is preferably adjusted to suit the polymerase being used. Long primer spacing is preferred when using a polymerase with a rapid polymerization rate. Shorter primer spacing is preferred when using a polymerase with a slower polymerization rate. The following assay can be used to determine optimal spacing with any polymerase. The assay uses sets of primers, with each set made up of 5 left primers and 5 right primers. The sets of primers are designed to hybridize adjacent to the same target sequence with each of the different sets of primers having a different primer spacing. The spacing is varied systematically between the sets of primers in increments of 25 nucleotides within the range of 25 nucleotides to 400 nucleotides (the spacing of the primers within each set is the same). A series of reactions are performed in which the same target sequence is amplified using the different sets of primers. The spacing that produces the highest experimental yield of DNA is the optimal primer spacing for the specific DNA polymerase, or DNA polymerase plus accessory protein combination being used.

DNA replication initiated at the sites in the target sequence where the primers hybridize will extend to and displace strands being replicated from primers hybridized at adjacent sites. Displacement of an adjacent strand makes it available for hybridization to another primer and subsequent initiation of another round of replication. The region(s) of the target sequence to which the primers hybridize is referred to as the hybridization target of the target sequence. The top panel of FIG. 1 illustrates one of the preferred relationships of a set of primers to a target sequence and to the amplification target of the target sequence.

A set of primers can include any desired number of primers of different nucleotide sequence. For MSDA, it is preferred that a set of primers include a plurality of primers. It is more preferred that a set of primers include 3 or more primers. It is still more preferred that a set of primers include 4 or more, 5 or more, 6 or more, or 7 or more primers. In general, the more primers used, the greater the level of amplification that will be obtained. There is no fundamental upper limit to the number of primers that a set of primers can have. However, for a given target sequence, the number of primers in a set of primers will generally be limited to number of hybridization sites available in the target sequence. For example, if the target sequence is a 10,000 nucleotide DNA molecule and 20 nucleotide primers are used, there are 500 non-overlapping 20 nucleotide sites in the target sequence. Even more primers than this could be used if overlapping sites are either desired or acceptable. It is preferred that a set of primers include no more than about 300 primers. It is preferred that a set of primers include no more than about 200 primers. It is still more preferred that a set of primers include no more than about 100 primers. It is more preferred that a set of primers include no more than about 50 primers. It is most preferred that a set of primers include from 7 to about 50 primers. Any combination of the preferred upper and lower limits for the number of primers in a set of primers described above are specifically contemplated, including all intermediate ranges.

A preferred form of primer set for use in MSDA includes two sets of primers, referred to as a right set of primers and a left set of primers. The right set of primers and left set of primers are designed to be complementary to opposite strands of a target sequence. It is preferred that the complementary portions of the right set primers are each complementary to the right hybridization target, and that each is complementary to a different portion of the right hybridization target. It is preferred that the complementary portions of the left set primers are each complementary to the left hybridization target, and that each is complementary to a different portion of the left hybridization target. The right and left hybridization targets flank opposite ends of the amplification target in a target sequence. A preferred form of these relationships are illustrated in the top panel of FIG. 1. It is preferred that a right set of primers and a left set of primers each include a preferred number of primers as described above for a set of primers. Specifically, it is preferred that a right or left set of primers include a plurality of primers. It is more preferred that a right or left set of primers include 3 or more primers. It is still more preferred that a right or left set of primers include 4 or more, 5 or more, 6 or more, or 7 or more primers. It is preferred that a right or left set of primers include no more than about 200 primers. It is more preferred that a right or left set of primers include no more than about 100 primers. It is most preferred that a right or left set of primers include from 7 to about 100 primers. Any combination of the preferred upper and lower limits for the number of primers in a set of primers described above are specifically contemplated, including all intermediate ranges. It is also preferred that, for a given target sequence, the right set of primers and the left set of primers include the same number of primers. It is also preferred that, for a given target sequence, the right set of primers and the left set of primers are composed of primers of similar length and/or hybridization characteristics.

Primers for Whole Genome Strand Displacement Amplification: In the case of whole genome strand displacement amplification, it is preferred that a set of primers having random or partially random nucleotide sequences be used. In a nucleic acid sample of significant complexity, which is the referred target sequence for WGSDA, specific nucleic acid sequences present in the sample need not be known and the primers need not be designed to be complementary to any particular sequence. Rather, the complexity of the nucleic acid sample results in a large number of different hybridization target sequences in the sample which will be complementary to various primers of random or partially random sequence. The complementary portion of primers for use in WGSDA can be fully randomized, have only a portion that is randomized, or be otherwise selectively randomized.

The number of random base positions in the complementary portion of primers are preferably from 20% to 100% of the total number of nucleotides in the complementary portion of the primers. More preferably the number of random base positions are from 30% to 100% of the total number of nucleotides in the complementary portion of the primers. Most preferably the number of random base positions are from 50% to 100% of the total number of nucleotides in the complementary portion of the primers. Sets of primers having random or partially random sequences can be synthesized using standard techniques by allowing the addition of any nucleotide at each position to be randomized. It is also preferred that the sets of primers are composed of primers of similar length and/or hybridization characteristics.

Primers for Multiple Strand Displacement Amplification On Concatenated DNA: For multiple strand displacement amplification of concatenated DNA, a set of primers having random or partially random nucleotide sequences can be used. In a nucleic acid sample of significant complexity, such as DNA concatenated from a mixture of many sequences, specific nucleic acid sequences present in the sample need not be known and the primers need not be designed to be complementary to any particular sequence. Rather, the complexity of the nucleic acid sample results in a large number of different hybridization target sequences in the sample which will be complementary to various primers of random or partially random sequence. The complementary portion of primers for use in MSDA-CD can be fully randomized, have only a portion that is randomized, or be otherwise selectively randomized.

The number of random base positions in the complementary portion of primers are preferably from 20% to 100% of the total number of nucleotides in the complementary portion of the primers. More preferably the number of random base positions are from 30% to 100% of the total number of nucleotides in the complementary portion of the primers. Most preferably the number of random base positions are from 50% to 100% of the total number of nucleotides in the complementary portion of the primers. Sets of primers having random or partially random sequences can be synthesized using standard techniques by allowing the addition of any nucleotide at each position to be randomized. It is also preferred that the sets of primers are composed of primers of similar length and/or hybridization characteristics.

Where the DNA has been concatenated with linkers, amplification can be performed using primers complementary to sequences in the linkers. This is the preferred form of MSDA-CD. It is preferred that the complementary portion of each primer is designed to be complementary to sequences in the linkers. It is preferred that primers for use with linker-concatenated DNA include primers complementary to both strands of the linker sequence. This is illustrated in FIG. 4. It is also preferred that the primers are not complementary to each other. This prevents the primers from hybridizing to each other. If the linkers used to concatenate the DNA are sufficiently long, a set of primers complementary to different portions of the linker sequence can be used. This is equivalent to the situation in MSDA, and the sets of primers can be designed and used in the same manner as discussed for MSDA primer sets. Random primers can be used to amplify concatenated DNA whether or not linkers have been used to concatenate the DNA.

It is preferred that the target sequences for use in MSDA, WGSDA, and MSDA-CD are not, or are not part of, nucleic acid molecules made up of multiple tandem repeats of a sequence. It is more preferable that the target sequences are not, or are not part of, nucleic acid molecules made up of multiple tandem repeats of a single sequence. It is most preferred that the target sequences are not, or are not part of, nucleic acid molecules made up of multiple tandem repeats of a single sequence that were synthesized by rolling circle replication. An example of such tandem repeat DNA made by rolling circle replication is the tandem sequence DNA described in WO 97/19193. DNA concatenated from identical or nearly identical DNA fragments is not made by rolling circle replication and so is not a nucleic acid molecule made up of multiple tandem repeats of a single sequence that was synthesized by rolling circle replication. Thus, although it is preferred that the target sequences are not nucleic acid molecules made up of multiple tandem repeats of a single sequence, some such target sequences, such as DNA concatenated from identical or nearly identical DNA fragments, are preferred over, and to the exclusion of, nucleic acid molecules made up of multiple tandem repeats of a single sequence that are synthesized by rolling circle replication (such as the tandem sequence DNA described in WO 97/19193). It is preferred that target sequences for the disclosed method are not produced by the methods described in WO 97/19193.

Detection Tags: The non-complementary portion of a primer can include sequences to be used to further manipulate or analyze amplified sequences. An example of such a sequence is a detection tag, which is a specific nucleotide sequence present in the non-complementary portion of a primer. Detection tags have sequences complementary to detection probes. Detection tags can be detected using their cognate detection probes. Detection tags become incorporated at the ends of amplified strands. The result is amplified DNA having detection tag sequences that are complementary to the complementary portion of detection probes. If present, there may be one, two, three, or more than three detection tags on a primer. It is preferred that a primer have one, two, three or four detection tags. Most preferably, a primer will have one detection tag. Generally, it is preferred that a primer have 10 detection tags or less. There is no fundamental limit to the number of detection tags that can be present on a primer except the size of the primer. When there are multiple detection tags, they may have the same sequence or they may have different sequences, with each different sequence complementary to a different detection probe. It is preferred that a primer contain detection tags that have the same sequence such that they are all complementary to a single detection probe. For some multiplex detection methods, it is preferable that primers contain up to six detection tags and that the detection tag portions have different sequences such that each of the detection tag portions is complementary to a different detection probe. A similar effect can be achieved by using a set of primers where each has a single different detection tag. The detection tags can each be any length that supports specific and stable hybridization between the detection tags and the detection probe. For this purpose, a length of 10 to 35 nucleotides is preferred, with a detection tag portion 15 to 20 nucleotides long being most preferred.

Address Tag: Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. It is preferred that a primer have one or two address tags. Most preferably, a primer will have one address tag. Generally, it is preferred that a primer have 10 address tags or less. There is no fundamental limit to the number of address tags that can be present on a primer except the size of the primer. When there are multiple address tags, they may have the same sequence or they may have different sequences, with each different sequence complementary to a different address probe. It is preferred that a primer contain address tags that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

C. Linkers

As used herein for concatenating DNA, a linker is a small, double-stranded DNA molecule. For MSDA-CD, linkers serve two main purposes; facilitating concatenation of DNA fragments and facilitating amplification. For the first purpose, linkers are generally designed to have ends compatible with the ends of the DNA fragments to be concatenated. For example, if the DNA fragments have blunt ends (or the ends will be made blunt), blunt ended linkers would be used. For DNA fragments that have been tailed with one or more nucleotides, the linkers should have a complementary tail. An example of such tailing is the addition of single adenosine residues to the 3' ends of cDNA. For facilitating amplification, linkers should have one or more sequences complementary to primers to be used in MSDA-CD. Such sequences are referred to as primer complement portions of the linkers. Primer complement portions of linkers are complementary to complementary portions of primers. A primer complement portion can have an arbitrary sequence so long as it is complementary to the portion of the intended primer. If there are primer complement portions on opposite strands of the linker, they should not overlap. The primer can also have one or more restriction enzyme cleavage sites. Such restriction sites allow the amplified DNA to be cut into fragments, and preferably into fragments representing the original DNA fragments which were concatenated. For this purpose, it is preferred that a rare restriction site be used (for example, an eight-base recognition site). An example of the structure of a linker of this type is illustrated below.

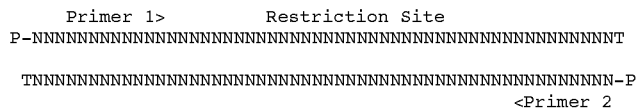

Linkers can also contain one or more promoter sequences. Such promoter sequences allow the amplified DNA to be further amplified by transcription after MSDA-CD. If two promoters are incorporated into the linker, they are preferably located on different strands of the linker. An example of a linker, having a single protruding thymidine residue at both 3' termini, and a phosphate group at both 5' termini, is illustrated below (P indicates phosphate).

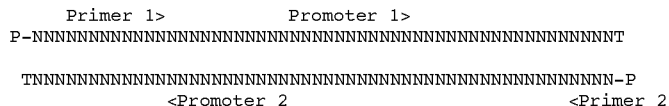

The promoter and primer sequences may be arranged in any order, but the arrangement shown above is preferred. Any number of primers and promoters may be used. However, it is preferred that, where the DNA to be concatenated is cDNA, promoters be incorporated into the cDNA as part of the primers used for cDNA synthesis (Lockhart et al.).

D. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccirtimide ester) and rhodamine (5,6-etramethyl rhodamine). Preferred fluorescent labels are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a preferred form of detection label since they can be directly incorporated into the amplification products during synthesis. Examples of detection labels that can be incorporated into amplified DNA or RNA include nucleotide analogs such as BrdUrd (Hoy and Schimke, Mutation Research 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-ioxetane-3-2'-(51'-chloro)tricyclo [$3.3.1.1^{3.7}$]decane]-4-yl) phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588–1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

E. Detection Probes

Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnol.* 14:303–309 (1995)). The use of such probes eliminates the need for removal of unhybridized probes prior to label detection because the unhybridized detection probes will not produce a signal. This is especially useful in multiplex assays.

F. Address Probes

An address probe is an oligonucleotide having a sequence complementary to address tags on primers. The complementary portion of an address probe can be any length that supports specific and stable hybridization between the address probe and the address tag For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

G. Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik el al., *Nucleic Acids Res.* 18:6409–6412 (1990).

H. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a microtiter plate multiplex assay, address probes specific for up to 96 different amplified nucleic acids (each representing a different target sequence amplified via a different set of primers) can be immobilized on a microtiter plate, each in a different well. Capture and detection will occur only in those wells corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

I. Solid-State Samples

Solid-state samples are solid-state substrates or supports to which target sequences have been coupled or adhered. Target sequences are preferably delivered in a target sample or assay sample. A preferred form of solid-state sample is an array sample. An array sample is a solid-state sample to which multiple different target sequences have been coupled or adhered in an array, grid, or other organized pattern.

Solid-state substrates for use in solid-state samples can include any solid material to which target sequences can be coupled or adhered. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, slides, fibers, woven fibers, shaped polymers, particles and microparticles.

Preferred forms for a solid-state substrate are microtiter dishes and glass slides. The most preferred form of microtiter dish is the standard 96-well type.

Target sequences immobilized on a solid-state substrate allow formation of target-specific amplified nucleic acid localized on the solid-state substrate. Such localization provides a convenient means of washing away reaction components that might interfere with subsequent detection steps, and a convenient way of assaying multiple different samples simultaneously. Amplified nucleic acid can be independently formed at each site where a different sample is adhered. For immobilization of target sequences or other oligonucleotide molecules to form a solid-state sample, the methods described above for can be used.

A preferred form of solid-state substrate is a glass slide to which up to 256 separate target samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487–470 (1995). Briefly, microarrays can be fabricated on poly-L-lysine-coated microscope slides (Sigma) with an arraying machine fitted with one printing tip. The tip is loaded with 1$\mu$l of a DNA sample (0.5 mg/ml) from, for example, 96-well microtiter plates and deposited ~0.005 $\mu$l per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

J. DNA Polymerases

DNA polymerases useful in the multiple displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are Bst large fragment DNA polymerase (Exo(-) Bst; Aliotta et al., *Genet. Anal.* (*Netherlands*) 12:185–20 195 (1996)) and exo(-)Bca DNA polymerase (Walker and Linn, *Clinical Chemistry* 42:1604–1608 (1996)). Other useful polymerases include bacteriophage $\phi$29 DNA polymerase (U.S. Pat. Nos. 5,198,543 and 5,001,050 to Blanco et al.), phage M2 DNA polymerase (Matsumoto et al., *Gene* 84:247 (1989)), phage $\phi$PRD1 DNA polymerase (Jung et al., *Proc. Natl. Acad. Sci. USA* 84:8287 (1987)), exo(-)VENT® DNA polymerase (Kong et al., *J. Biol. Chem.* 268:1965–1975 (1993)), Klenow fragment of DNA polymerase I (Jacobsen el al., *Eur. J.*

*Biochem.* 45:623–627 (1974)), T5 DNA polymerase (Chatterjee et al., *Gene* 97:13–19 (1991)), Sequenase (U.S. Biochemicals), PRD1 DNA polymerase (Zhu and Ito, *Biochim. Biophys. Acta.* 1219:267–276 (1994)), and T4 DNA polymerase holoenzyme (Kaboord and Benkovic, *Curr. Biol.* 5:149–157 (1995)). Exo(-)Bst DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes sirnplex viral protein ICP8 (Boehmer and Lehnan, *J. Virology* 67(2):711–715 (1993); Skaliter and Lehman, *Proc. Natl. Acad. Sci. USA* 91(22):10665–10669 (1994)); single-stranded DNA binding proteins (SSB; Rigler and Romano, *J. Biol. Chem.* 270:8910–8919 (1995)); phage T4 gene 32 protein (Villemain and Giedroc, *Biochemistry* 35:14395–14404 (1996); and calf thymus helicase (Siegel et al., *J. Biol. Chem.* 267:13629–13635 (1992)).

The ability of a polymerase to carry out strand displacement replication can be determined by using the polymerase in a strand displacement replication assay such as those described in Examples 1 and 2. The assay in the examples can be modified as appropriate. For example, a helicase can be used instead of SSB. Such assays should be performed at a temperature suitable for optimal activity for the enzyme being used, for example, 32° C. for φ29 DNA polymerase, from 46° C. to 64° C. for exo(-) Bst DNA polymerase, or from about 60° C. to 70° C. for an enzyme from a hyperthermophylic organism. For assays from 60° C. to 70° C., primer length may be increased to 20 bases for random primers, or to 22 bases for specific primers. Another useful assay for selecting a polymerase is the primer-block assay described in Kong et al., *J. Biol. Chem.* 268:1965–1975 (1993). The assay consists of a primer extension assay using an M13 ssDNA template in the presence or absence of an oligonucleotide that is hybridized upstream of the extending primer to block its progress. Enzymes able to displace the blocking primer in this assay are useful for the disclosed method.

The materials described above can be packaged together in any suitable combination as a kit useful for performing the disclosed method.

II. METHOD

The disclosed method is based on strand displacement replication of the nucleic acid sequences by multiple primers. The method can be used to amplify one or more specific sequences (multiple strand displacement amplification), an entire genome or other DNA of high complexity (whole genome strand displacement amplification), or concatenated DNA (multiple strand displacement amplification of concatenated DNA). The disclosed method generally involves hybridization of primers to a target nucleic acid sequence and replication of the target sequence primed by the hybridized primers such that replication of the target sequence results in replicated strands complementary to the target sequence. During replication, the growing replicated strands displace other replicated strands from the target sequence (or from another replicated strand) via strand displacement replication. Examples of such displacement of replicated strands are illustrated in the figures. As used herein, a replicated strand is a nucleic acid strand resulting from elongation of a primer hybridized to a target sequence or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of a target sequence to be made in a single, isothermic reaction.

A. Multiple Strand Displacement Amplification

In one preferred form of the method, referred to as multiple strand displacement amplification (MSDA), two sets of primers are used, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The 5' end of primers in both sets are distal to the nucleic acid sequence of interest when the primers are hybridized to the flanking sequences in the nucleic acid molecule. Preferably, each member of each set has a portion complementary to a separate and non-overlapping nucleotide sequence flanking the target nucleotide sequence. Amplification proceeds by replication initiated at each primer and continuing through the target nucleic acid sequence. A key feature of this method is the displacement of intervening primers during replication. Once the nucleic acid strands elongated from the right set of primers reaches the region of the nucleic acid molecule to which the left set of primers hybridizes, and vice versa, another round of priming and replication will take place. This allows multiple copies of a nested set of the target nucleic acid sequence to be synthesized in a short period of time.

Multiple strand displacement amplification can be performed by (a) mixing a set of primers with a target sample, to produce an primer-target sample mixture, and incubating the primer-target sample mixture under conditions that promote hybridization between the primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence. Strand displacement replication is preferably accomplished by using a strand displacing DNA polymerase or a DNA polymerase in combination with a compatible strand displacement factor. A preferred example of MSDA is illustrated in FIG. 1. Another example of MSDA is illustrated in FIG. 3.

By using a sufficient number of primers in the right and left sets, only a few rounds of replication are required to produce hundreds of thousands of copies of the nucleic acid sequence of interest. For example, it can be estimated that, using right and left primer sets of 26 primers each, 200,000 copies of a 5000 nucleotide amplification target can be produced in 10 minutes (representing just four rounds of priming and replication). It can also be estimated that, using right and left primer sets of 26 primers each, 200,000 copies of a 47,000 nucleotide amplification target can be produced in 60 minutes (again representing four rounds of priming and replication). These calculations are based on a polymerase extension rate of 50 nucleotides per second. It is emphasized that reactions are continuous and isothermal—no cycling is required.

The disclosed method has advantages over the polymerase chain reaction since it can be carried out under isothermal conditions. No thermal cycling is needed because the polymerase at the head of an elongating strand (or a compatible strand-displacement factor) will displace, and thereby make available for hybridization, the strand ahead of it. Other advantages of multiple strand displacement amplification include the ability to amplify very long nucleic acid segments (on the order of 50 kilobases) and rapid amplification of shorter segments (10 kilobases or less). Long nucleic acid segments can be amplified in the disclosed method since there no cycling which could interrupt continuous synthesis or allow the formation of artifacts due to rehybridization of replicated strands. In multiple strand displacement amplification, single priming events at unintended sites will not lead to artifactual amplification at these sites (since amplification at the intended site will quickly outstrip the single strand replication at the unintended site).

B. Whole Genome Strand Displacement Amplification

In another preferred form of the method, referred to as whole genome strand displacement amplification (WGSDA), a random or partially random set of primers is used to randomly prime a sample of genomic nucleic acid (or another sample of nucleic acid of high complexity). By choosing a sufficiently large set of primers of random or mostly random sequence, the primers in the set will be collectively, and randomly, complementary to nucleic acid sequences distributed throughout nucleic acid in the sample. Amplification proceeds by replication with a processive polymerase initiated at each primer and continuing until spontaneous termination. A key feature of this method is the displacement of intervening primers during replication by the polymerase. In this way, multiple overlapping copies of the entire genome can be synthesized in a short time. It can be estimated that, in a WGSDA on a genomic sample, after 180 minutes of incubation each primer will have been elongated by, on average, 55,000 bases. By using a sufficiently high concentration of primers, additional priming events on replicated strands will result in additional rounds of copying. It can be estimated that after 180 minutes 400 copies of the entire genome will have been produced.

Figure 2:
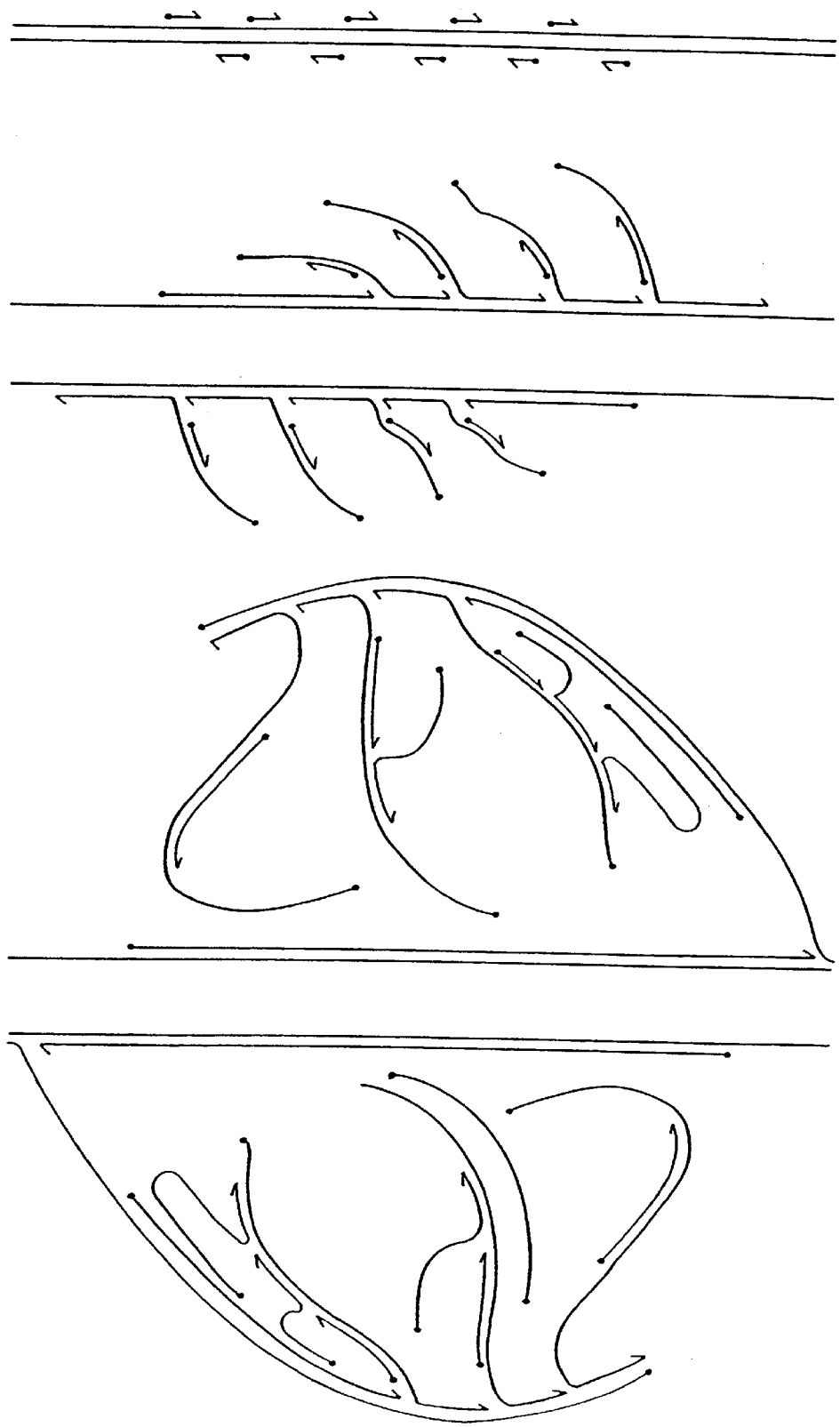
FIG. 2 is a diagram of an example of whole genome strand displacement amplification (WGSDA). At the top is a diagrammatical representation of genomic DNA. Hybridized to the nucleic acid molecule are primers from a set of random or partially random primers (the primer lengths are not intended to be to scale). For simplicity, only a portion of one molecule of genomic DNA is depicted. Diagramed in the middle are the multiple strands of replicated nucleic acid being elongated from each primer. The polymerase at the end of each elongating strand displaces the elongating strand of any primer it encounters. Also shown additional primers from the set of random or partially random primers which hybridize to complementary sites on the newly replicated strands. The newly replicated strands are made available for hybridization to the primers through displacement by the polymerase elongating a following strand. Diagramed at the bottom are the multiple strands of replicated nucleic acid further elongated. For simplicity only four of the originally synthesized strands (two on the upper target sequence strand and two on the lower target sequence strand) are depicted in the bottom panel.

Whole genome strand displacement amplification can be performed by (a) mixing a set of random or partially random primers with a genomic sample (or other nucleic acid sample of high complexity), to produce an primer-target sample mixture, and incubating the primer-target sample mixture under conditions that promote hybridization between the primers and the genomic DNA in the primer-target sample mixture, and (b) mixing DNA polymerase with the primer-target sample mixture, to produce a polymerase-target sample mixture, and incubating the polymerase-target sample mixture under conditions that promote replication of the genomic DNA. Strand displacement replication is preferably accomplished by using a strand displacing DNA polymerase or a DNA polymerase in combination with a compatible strand displacement factor. WGSDA is illustrated in FIG. 2.

The method has advantages over the polymerase chain reaction since it can be carried out under isothermal conditions. Other advantages of whole genome strand displacement amplification include a higher level of amplification than whole genome PCR (up to 5 times higher), amplification is less sequence-dependent than PCR, and there are no re-annealing artifacts or gene shuffling artifacts as can occur with PCR (since there are no cycles of denaturation and re-annealing).

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction.

It is preferred that the set of primers used for WGSDA be used at concentrations that allow the primers to hybridize at desired intervals within the nucleic acid sample. For example, by using a set of primers at a concentration that allows them to hybridize, on average, every 4000 to 8000 bases, DNA replication initiated at these sites will extend to and displace strands being replicated from adjacent sites. It should be noted that the primers are not expected to hybridize to the target sequence at regular intervals. Rather, the average interval will be a general function of primer concentration.

As in multiple strand displacement amplification, displacement of an adjacent strand makes it available for hybridization to another primer and subsequent initiation of another round of replication. The interval at which primers in the set of primers hybridize to the target sequence determines the level of amplification. For example, if the average interval is short, adjacent strands will be displaced quickly and frequently. If the average interval is long, adjacent strands will be displaced only after long runs of replication.

In the disclosed method, the DNA polymerase catalyzes primer extension and strand displacement in a processive strand displacement polymerization reaction that proceeds as long as desired, generating molecules of up to 60,000 nucleotides or larger. Preferred strand displacing DNA polymerases are large fragment Bst DNA polymerase (Exo(-) Bst), exo(-)Bca DNA polymerase, the DNA polymerase of the bacteriophage φ29 and Sequenase. During strand displacement replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Genome amplification using PCR, and uses for the amplified DNA, is described in Zhang et al., *Proc. Natl. Acad. Sci. USA* 89:5847–5851 (1992), Telenius et al., *Genomics* 13:718–725 (1992), Cheung et al., *Proc. Natl. Acad. Sci. USA* 93:14676–14679 (1996), and Kukasjaarvi et al., *Genes, Chromosomes and Cancer* 18:94–101 (1997). The uses of the amplified DNA described in these publications are also generally applicable to DNA amplified using the disclosed methods. Whole Genome Strand Displacement Amplification, unlike PCR-based whole genome amplification, is suitable for haplotype analysis since WGSDA yields longer fragments than PCR-based whole genome amplification. PCR-based whole genome amplification is also less suitable for haplotype analysis since each

C. Multiple Strand Displacement Amplification of Concatenated DNA

In another preferred form of the method, referred to as multiple strand displacement amplification of concatenated DNA (MSDA-CD), concatenated DNA is amplified. A preferred form of concatenated DNA is concatenated cDNA. Concatenated DNA can be amplified using a random or partially random set of primers, as in WGSDA, or using specific primers complementary to specific hybridization targets in the concatenated DNA. MSDA-CD is preferred for amplification of a complex mixture or sample of relatively short nucleic acid samples (that is, fragments generally in the range of 100 to 6,000 nucleotides). Messenger RNA is the most important example of such a complex mixture. MSDA-CD provides a means for amplifying all cDNAs in a cell is equal fashion. Because the concatenated cDNA can be amplified up to 5,000-fold, MSDA-CD will permit RNA profiling analysis based on just a few cells. To perform MSDA-CD, DNA must first be subjected to a concatenation step. If an RNA sample (such as mRNA) is to be amplified, the RNA is first converted to a double-stranded cDNA using standard methods. The cDNA, or any other set of DNA fragments to be amplified, is then converted into a DNA concatenate, preferably with incorporation of linkers.

DNA fragments can be concatenated by ligation using standard conditions. The state of the ends of the DNA fragments, such as blunt, staggered or ragged, should be taken into account when concatenating DNA. For example, staggered ends, such as those produced by digestion with restriction enzymes, can be used to mediate concatenation if the overhanging sequences are compatible. DNA with ragged or staggered ends can be made blunt ended prior to ligation. All of these operations are well known and of general use. If linkers are used, the linkers can either be ligated to blunt ended DNA (using blunt ended linkers), or to DNA having compatible overhanging ends, in which case the linkers can be in the form of adaptors.

The following illustrates an example of how the MSDA-CD can be used to amplify mRNA sequences. First, cDNA is made from the mRNA of interest. In this example, the cDNA is made in such a way that it contains phosphorylated 5'-ends. The cDNA is then tailed with a single adenosine residue at both 3' ends using Taq DNA polymerase (as described, for example, by Brownstein et al., *Biotechniques* 20:1004–1010 (1996), and in the catalog of Research Genetics, Inc.). The A-tailed cDNA is then mixed with the T-tailed linkers in the presence of ATP and T4 DNA ligase in standard ligation buffer (see, for example, Holton and Graham, *Nucl. Acids Res.* 19:1156 (1991), and instructions for the use of pGEM-T vectors in the Promega Catalog (Promega Biotec, Madison, Wiss., 1997) page 206), and the reaction is incubated overnight at 16° C. to generate long concatenated DNA molecules. The concatenated molecules consist of tandemly ligated cDNAs and linkers, in alternating order, of the structure —linker—DNA—linker—DNA—linker—DNA—. The A-tailing and T-tailing method is just one example of many possible methods to obtain tandem, concatenated ligation of linkers and DNA fragments. It is also possible to concatenate DNA fragments without linkers to obtain concatenated molecules of the structure—DNA—DNA—DNA—DNA—. Concatenated DNA fragments with linkers is referred to herein as linker-concatenated DNA or linker-DNA concatenates. Concatenated DNA fragments without linkers is referred to herein as nonlinker-concatenated DNA or nonlinker-DNA concatenates. The terms concatenated DNA and DNA concatenate refer to both linker-concatenated DNA and nonlinker-concatenated DNA. Amplification of linker-DNA concatenates is more specific and efficient than amplification of nonlinker-DNA concatenates, because specific primers can be directed to the linker sequence. Thus, the linker-DNA concatenation method is the preferred form of performing MSDA-CD.

It is preferred that the concatenated product be as long as possible.

This is so because the extent of DNA amplification obtainable with MSDA-CD within any time period is influenced by the length of the concatenated DNA. The longer the concatenated DNA is, and the more linkers it contains, the more efficient the amplification process will be. Concatenation is generally favored by ligating the fragments at high concentration.

An example of MSDA-CD performed on linker-concatenated DNA is illustrated in FIG. 4. Two different linker-specific primers were used that prime on different sequences on different strands of the linker. The two primers should not be complementary to each other. At the top of FIG. 4 is the double-stranded DNA concatenate with incorporated linkers. The DNA is denatured to make it single-stranded, and the two linker-specific primers are utilized to amplify the DNA by multiple strand displacement. It can be estimated that MSDA-CD will amplify a DNA sample as much as 5,000-fold. In the case of the mRNA profiling (Lockhart et al.), MSDA-CD, combined with transcriptional amplification, could be used to improve the limit of detection, permitting profiling analysis in samples containing only cells.

When using linker-concatenated DNA, multiple strand displacement amplification of concatenated DNA can be performed by (a) mixing primers with a concatenated DNA sample, to produce an primer-target sample mixture, and incubating the primer-target sample mixture under conditions that promote hybridization between the primers and the concatenated DNA in the primer-target sample mixture, and (b) mixing DNA polymerase with the primer-target sample mixture, to produce a polymerase-target sample mixture, and incubating the polymerase-target sample mixture under conditions that promote replication of the concatenated DNA. Strand displacement replication is preferably accomplished by using a strand displacing DNA polymerase or a DNA polymerase in combination with a compatible strand displacement factor.

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radio-active labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. Sequences in DNA amplified by MSDA-CD performed on concatenated DNA where the linkers or primers include promoter sequences can be further amplified by transcriptional amplification using the promoters.

Where the linkers used for concatenation include a restriction enzyme site, the amplified DNA can be fragmented by restriction enzyme digestion.

Cleavage of the amplified DNA can permit or simplify further processing and analysis of the amplified DNA. If the site used appears rarely (for example, eight-base recognition sites), the resulting fragments will represent the original DNA fragments that were concatenated.

When used, a random or partially random set of primers randomly prime the concatenated DNA. By choosing a sufficiently large set of primers of random or mostly random sequence, the primers in the set will be collectively, and randomly, complementary to nucleic acid sequences distributed throughout the concatenated DNA. Amplification proceeds by replication with a processive polymerase initiated at each primer and continuing until spontaneous termination. A key feature of this method is the displacement of intervening primers during replication by the polymerase. In this way, multiple overlapping copies of the entire concatenated DNA sample can be synthesized in a short time.

When using random or partially random primers, multiple strand displacement amplification of concatenated DNA can be performed by (a) mixing a set of random or partially random primers with a concatenated DNA sample, to produce an primer-target sample mixture, and incubating the primer-target sample mixture under conditions that promote hybridization between the primers and the concatenated DNA in the primer-target sample mixture, and (b) mixing DNA polymerase with the primer-target sample mixture, to produce a polymerase-target sample mixture, and incubating the polymerase-target sample mixture under conditions that promote replication of the concatenated DNA. MSDA-CD using random or partially random primers is similar to WGSDA and proceeds generally as illustrated in FIG. 2.

It is preferred that a set of random or partially random primers used for MSDA-CD be used at concentrations that allow the primers to hybridize at desired intervals within the nucleic acid sample. For example, by using a set of primers at a concentration that allows them to hybridize, on average, every 4000 to 8000 bases, DNA replication initiated at these sites will extend to and displace strands being replicated from adjacent sites. It should be noted that the primers are not expected to hybridize to the target sequence at regular intervals. Rather, the average interval will be a general function of primer concentration.

As in multiple strand displacement amplification, displacement of an adjacent strand makes it available for hybridization to another primer and subsequent initiation of another round of replication. The interval at which primers in the set of primers hybridize to the target sequence determines the level of amplification. For example, if the average interval is short, adjacent strands will be displaced quickly and frequently. If the average interval is long, adjacent strands will be displaced only after long runs of replication. For amplification of linker-concatenated DNA, where the primers are complementary to linker sequences, the size of the DNA fragments that were concatenated determines the spacing between the primers.

D. Modifications And Additional Operations

1. Detection of Amplification Products

Amplification products can be detected directly by, for example, primary labeling or secondary labeling, as described below.

(a) Primary Labeling

Primary labeling consists of incorporating labeled moieties, such as fluorescent nucleotides, biotinylated nucleotides, digoxygenin-containing nucleotides, or bromodeoxyuridine, during strand displacement replication.

For example, one may incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

(b) Secondary Labeling with Detection Probes

Secondary labeling consists of using suitable molecular probes, referred to as detection probes, to detect the amplified DNA or RNA. For example, primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand.

(c) Multiplexing and Hybridization Array Detection

Detection of amplified nucleic acids can be multiplexed by using sets of different primers, each set designed for amplifying different target sequences. Only those primers that are able to find their targets will give rise to amplified products. There are two alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the target sequence as an address tag.

(d) Enzyme-linked Detection

Amplified nucleic acid labeled by incorporation of labeled nucleotides can be detected with established enzyme-linked detection systems. For example, amplified nucleic acid labeled by incorporation of biotin-16-UTP (Boehringher Mannheim) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

2. Linear Strand Displacement Amplification

A modified form of multiple strand displacement amplification can be performed which results in linear amplification of a target sequence. This modified method is referred to as linear strand displacement amplification (LSDA) and is accomplished by using a set of primers where all of the primers are complementary to the same strand of the target sequence. In LSDA, as in MSDA, the set of primers hybridize to the target sequence and strand displacement amplification takes place. However, only one of the strands of the target sequence is replicated. LSDA requires thermal cycling between each round of replication to allow a new set of primers to hybridize to the target sequence. Such thermal cycling is similar to that used in PCR. Unlike linear, or single primer, PCR, however, each round of replication in LSDA results in multiple copies of the target sequence. One copy is made for each primer used. Thus, if 20 primers are used in LSDA, 20 copies of the target sequence will be made in each cycle of replication.

DNA amplified using MSDA and WGSDA can be further amplified by transcription. For this purpose, promoter sequences can be included in the non-complementary portion of primers used for strand displacement amplification, or in linker sequences used to concatenate DNA for MSDA-CD.

EXAMPLES

Example 1

Multiple Strand Displacement Amplification of Lambda DNA

This example illustrates multiple displacement amplification using a total of 14 primers, 7 in each of a right primer set and a left primer set. The primers in each set are designed to hybridize to opposite strands on each side of a region to be amplified.

1. The first step is a ligation to close nicks, insuring that long strands are available for copying. A total of 10 μg of Bacteriophage lambda DNA was dissolved in 100 μl of T4 ligase buffer (10 mM Tris, pH 7.5, 0.20 M NaCl, 10 mM MgCl$_2$, 2 mM ATP). T4 DNA ligase was added to a final concentration of 8 Units/μl, and the material was incubated for 1.5 hours at 37° C. in order to close any nicks in the DNA, making it perfectly double-stranded. The DNA solution was then diluted five-fold with distilled water, to yield a final DNA concentration of 20 ng/μl.

2. An aliquot of 1.5 μl of ligated lambda DNA (containing 30 ng of DNA) was mixed with 18.2 μl of distilled water, and a suitable multiple primer mixture (primers made by standard phosphoramidite chemistry). The primers used in this example are indicated below. The nomenclature is "PL" for left primers and "PR" for right primers. Seven left primers and seven right primers were used. For each set of 7 primers, the sequences are spaced 300 to 400 nucleotides between each other. The lambda DNA targeted by the primers is located within the region demarcated by map positions 39500 to 22000, and includes a total of approximately 17500 bases. This region encompasses lambda Hind II fragments of 2322 bp and 9416 bp.

Left Primers (5' to 3')

| | | | |
|---|---|---|---|
| 1 | GTTGATACATCAACTGCAC | PL7 | (SEQ ID NO:1) |
| 2 | CAATTACCTGAAGTCTTTC | PL6 | (SEQ ID NO:2) |
| 3 | TTGTCATATTGTATCATGC | PL5 | (SEQ ID NO:3) |
| 4 | AAGATGAAATAAGAGTAGC | PL4 | (SEQ ID NO:4) |
| 5 | TGCATGCTAGATGCTGATA | PL3 | (SEQ ID NO:5) |
| 6 | TATGACTGTACGCCACTGT | PL2 | (SEQ ID NO:6) |
| 7 | AGAGTTTCTTTGAGTAATC | PL1 | (SEQ ID NO:7) |

-continued
Right Primers (5' to 3')

| | | | |
|---|---|---|---|
| 1r | TTACAACCACTAAACCCAC | PR1 | (SEQ ID NO:8) |
| 2r | AATCGCCAGAGAAATCTAC | PR2 | (SEQ ID NO:9) |
| 3r | AGGGTTATGCGTTGTTCCA | PR3 | (SEQ ID NO:10) |
| 4r | TGTTAAGCAACGCACTCTC | PR4 | (SEQ ID NO:11) |
| 5r | AGTCTGGCGTAACCATCAT | PR5 | (SEQ ID NO:12) |
| 6r | AATAGTGTCTTTTGTGTCC | PR6 | (SEQ ID NO:13) |
| 7r | GCTTGTTACGGTTGATTTC | PR7 | (SEQ ID NO:14) |

Primers were added at a concentration such that in the following step (step 3, below) the final concentration of each primer was approximately 1 micromolar. The lambda DNA and primer mixture was heated at 95° C. for 2.5 minutes in order denature the lambda DNA, and the tube was immediately placed in ice.

3. The Multiple Strand Displacement Amplification reaction was set up at 0° C., in a volume of 30 μl, by adding to the tube of step 2 the following reagents, to give the final concentrations indicated below:

(a) 3 μl of 10X reaction buffer, designed to yield a final concentration of 40 mM Tris-HCl (pH 7.5), 25 mM NaCl, 8 mM MgCl$_2$, 6.7 mM DTT, 5% v/v DMSO (dimethylsulfoxide), and 400 μuM mM dATP, dGTP, dCTP, dTTP. Some MSDA reactions may work better at different concentration of DMSO, in the range of 1% to 7%.

(b) *E. coli* single-strand binding protein (SSB) to a final concentration of 1.4 μM.

(c) Sequenase 2.0 (Amersham Life Sciences) to a concentration of 0.475 units/μl (approximately 400 nM).

4. The reaction was incubated at 37° C. for 45 minutes. The DNA was amplified about 45-fold.

If desired, the amplified DNA can incubated anywhere from 2 to 24 hours at 55° C. in a buffer containing 30 mM Tris-HCl (pH 8.2), 150 mM NaCl, 1 mM EDTA, in order to permit most of the remaining single-stranded material to renature. The amplification yield can be increased by using more primers on each side of the DNA region to be-amplified. A suitable number of primers for this may be in the range of 10 to 30 primers on each side of desired DNA domain. Primer numbers exceeding 24 on each side may increase the frequency of nonspecific amplification.

Example 2

Whole Genome Amplification of Human DNA

This example is for whole genome amplification, as performed for the amplification of the human genome using random primers.

1. DNA was extracted from peripheral blood lymphocytes using a standard proteinase K digestion, followed by extraction with phenol/chloroform. The DNA was quantitated using the Pico-Green dye method (Molecular Probes, Inc., Eugene, Oreg.; Kit P-7589) and the material is then diluted in TE-0.2 buffer (10 mM Tris pH 8.3, 0.2 mM EDTA), to yield a final DNA concentration of 1 ng/μl.

2. Four microliters (4 nanograms) of human DNA and 20 μl of TE-0.2 buffer were mixed in a 500 μl microcentrifuge tube and denatured at 97° C. for 5 minutes. The tube was then immediately placed in ice.

3. An amplification reaction was set up in an ice bath, in a volume of 30 μl, by adding to the tube of step 2 the following reagents, to give the final concentrations indicated below:

(a) 3 µl of 10X reaction buffer, designed to yield a final concentration of 25 mM Tris-HCl (pH 8.8), 10 mM KCl, 10 mM $(NH_4)_2SO_4$, 2 mM $MgSO_4$, 0.1% Triton X-100, 5% v/v DMSO (dimethylsulfoxide), and 400 µM mM dATP, dGTP, dCTP, dTTP.

(b) A random DNA oligonucleotide primer of 20 bases in length to a final concentration of 4.0 µMolar.

(c) Phage T4 Gene 32 protein added to a final concentration of 30 ng/µl.

(d) Bst DNA polymerase large fragment (New England Biolabs), added last, at a final concentration of 0.35 units/µl.

4. The reaction was incubated at 48° C. for 4 hours, and stopped by addition of EDTA (final concentration 4 mM).

All publications cited herein are hereby incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of amplifying a target nucleic acid sequence, the method comprising, bringing into contact a set of primers, DNA polymerase, and a target sample, and incubating the target sample under conditions that promote replication of the target sequence, wherein replication of the target sequence results in replicated strands, wherein during replication at least one of the replicated strands is displaced from the target sequence by strand displacement replication of another replicated strand, wherein the set of primers has 3 or more primers complementary to the same strand of the target sequence.

2. The method of claim 1 wherein the DNA polymerase is φ29 DNA polymerase.

3. The method of claim 1 wherein the target sequence comprises two strands, wherein the set of primers has 3 or more primers complementary to one of the strands of the target sequence and the set of primers also has at least one primer complementary to the other strand of the target sequence.

4. The method of claim 1 wherein the target sequence comprises an amplification target and a hybridization target, wherein the hybridization target flanks the amplification target, wherein the set of primers comprises a plurality of primers, wherein each primer comprises a complementary portion, wherein the complementary portions of the primers are each complementary to a different portion of the hybridization target.

5. The method of claim 1 further comprising incubating the polymerase-target sample mixture under conditions that promote strand displacement.

6. The method of claim 1 wherein the set of primers has 4 or more primers complementary to the same strand of the target sequence.

7. The method of claim 1 wherein the set of primers has 4 or more primers.

8. The method of claim 7 wherein the set of primers has 5 or more primers.

9. The method of claim 1 wherein the conditions that promote replication of the target sequence are substantially isothermic.

10. The method of claim 1 wherein the conditions that promote replication of the target sequence do not involve thermal cycling.

11. The method of claim 1 wherein the conditions do not include thermal cycling.

12. The method of claim 4 wherein the set of primers comprises a right set of primers and a left set of primers,
wherein the target sequence is double-stranded, having a first and a second strand,
wherein the hybridization target comprises a right and left hybridization target, wherein the right hybridization target flanks the amplification target on one end and the left hybridization target flanks the amplification target on the other end,
wherein the complementary portions of the right set primers are (i) all complementary to the first strand of the target sequence and (ii) each complementary to a different portion of the right hybridization target, and
wherein the complementary portions of the left set primers are (i) all complementary to the second strand of the target sequence and (ii) each complementary to a different portion of the left hybridization target.

13. The method of claim 12 wherein the right and left set of primers each have 3 or more primers.

14. The method of claim 13 wherein the right and left set of primers each have 4 or more primers.

15. The method of claim 14 wherein the right and left set of primers each have 5 or more primers.

16. The method of claim 12 wherein the right and left set of primers each have the same number of primers.

17. The method of claim 1 wherein the target sequence is a nucleic acid sample of substantial complexity, and wherein the set of primers comprises primers having random nucleotide sequences.

18. The method of claim 17 wherein the target sequence is a sample of genomic nucleic acid.

19. The method of claim 17 wherein the primers are from 12 to 60 nucleotides in length.

20. The method of claim 19 wherein the primers are from 12 to 40 nucleotides in length.

21. The method of claim 20 wherein the primers are from 15 to 40 nucleotides in length.

22. The method of claim 21 wherein the primers are from 15 to 25 nucleotides in length.

23. The method of claim 17 wherein the primers are all of the same length.

24. The method of claim 17 wherein each primer comprises a constant portion and a random portion, wherein the constant portion of each primer has the same nucleotide sequence and the random portion of each primer has a random nucleotide sequence.

25. The method of claim 1 wherein the target sequence is concatenated DNA.

26. The method of claim 25 wherein the concatenated DNA is concatenated with linkers.

27. The method of claim 26 wherein each linker comprises a primer complement portion, wherein each primer comprises a complementary portion, wherein the complementary portion of each primer is complementary to the complementary portion of the linkers.

28. The method of claim 25 wherein the set of primers comprises primers having random nucleotide sequences.

29. The method of claim 28 wherein each primer comprises a constant portion and a random portion, wherein the constant portion of each primer has the same nucleotide sequence and the random portion of each primer has a random nucleotide sequence.

30. The method of claim 25 wherein the concatenated DNA is formed by ligating DNA fragments together.

31. The method of claim 30 wherein the DNA fragments are cDNA made from mRNA.

32. The method of claim 31 wherein the mRNA comprises a mixture of mRNA isolated from cells.

33. The method of claim 1 wherein the target sequence is not a nucleic acid molecule made up of multiple tandem repeats of a single sequence that was synthesized by rolling circle replication.

34. A method of amplifying a target nucleic acid sequence, the method comprising,
(a) mixing a set of primers with a target sample, to produce a primer-target sample mixture, and incubating the primer-target sample mixture under conditions that promote hybridization between the primers and the target sequence in the primer-target sample mixture,
(b) mixing DNA polymerase with the primer-target sample mixture, to produce a polymerase-target sample mixture, and incubating the polymerase-target sample mixture under conditions that promote replication of the target sequence, wherein the DNA polymerase is φ29 DNA polymerase,
wherein the set of primers comprises a right set of primers and a left set of primers,
wherein the target sequence is double-stranded, having a first and a second strand,
wherein the right set primers are all complementary to the first strand of the target sequence and the left set primers are all complementary to the second strand of the target sequence,
wherein the right set of primers has 4 or more primers and the left set of primers has 4 or more primers,
wherein replication of the target sequence results in replicated strands, wherein during replication at least one of the replicated strands is displaced from the target sequence by strand displacement replication of another replicated strand.

35. A method of amplifying a target nucleic acid sequence, the method comprising,
(a) mixing a set of primers with a target sample, to produce a primer-target sample mixture, and incubating the primer-target sample mixture under conditions that promote hybridization between the primers and the target sequence in the primer-target sample mixture,
(b) mixing DNA polymerase with the primer-target sample mixture, to produce a polymerase-target sample mixture, and incubating the polymerase-target sample mixture under conditions that promote replication of the target sequence, wherein the DNA polymerase is φ29 DNA polymerase,
wherein replication of the target sequence results in replicated strands, wherein during replication at least one of the replicated strands is displaced from the target sequence by strand displacement replication of another replicated strand,
wherein the target sequence is a nucleic acid sample of substantial complexity, and wherein the set of primers comprises primers having random nucleotide sequences.

36. A method of amplifying a target nucleic acid sequence, the method comprising,
(a) mixing a set of primers with a target sample, to produce a primer-target sample mixture, and incubating the primer-target sample mixture under conditions that promote hybridization between the primers and the target sequence in the primer-target sample mixture, (b) mixing DNA polymerase with the primer-target sample mixture, to produce a polymerase-target sample mixture, and incubating the polymerase-target sample mixture under conditions that promote replication of the target sequence, wherein the DNA polymerase is φ29 DNA polymerase, wherein all of the primers in the set of primers are complementary to the same strand in the target sequence, wherein the set of primers has 3 or more primers, wherein replication of the target sequence results in replicated strands, wherein during replication at least one of the replicated strands is displaced from the target sequence by strand displacement replication of another replicated strand.

37. A method of amplifying a target nucleic acid sequence, the method comprising, (a) mixing a set of primers with a target sample, to produce a primer-target sample mixture, and incubating the primer-target sample mixture under conditions that promote hybridization between the primers and the target sequence in the primer-target sample mixture, (b) mixing DNA polymerase with the primer-target sample mixture, to produce a polymerase-target sample mixture, and incubating the polymerase-target sample mixture under conditions that promote replication of the target sequence, wherein the DNA polymerase is φ29 DNA polymerase, wherein replication of the target sequence results in replicated strands, wherein during replication at least one of the replicated strands is displaced from the target sequence by strand displacement replication of another replicated strand, wherein the target sequence is a nucleic acid sample of substantial complexity, and wherein the set of primers comprises primers having random nucleotide sequences, wherein each primer comprises a constant portion and a random portion, wherein the constant portion of each primer has the same nucleotide sequence and the random portion of each primer has a random nucleotide sequence.

38. A method of amplifying a target nucleic acid sequence, the method comprising, (a) mixing a set of primers with a target sample, to produce a primer-target sample mixture, and incubating the primer-target sample mixture under conditions that promote hybridization between the primers and the target sequence in the primer-target sample mixture, (b) mixing DNA polymerase with the primer-target sample mixture, to produce a polymerase-target sample mixture, and incubating the polymerase-target sample mixture under conditions that promote replication of the target sequence, wherein the DNA polymerase is φ29 DNA polymerase, wherein replication of the target sequence results in replicated strands, wherein during replication at least one of the replicated strands is displaced from the target sequence by strand displacement replication of another replicated strand, wherein the conditions that promote replication of the target sequence do not involve thermal cycling, and wherein the target sequence is concatenated DNA.

39. A method of amplifying a target nucleic acid sequence, the method comprising, bringing into contact a set of primers, DNA polymerase, and a target sample, and incubating the target sample under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity, and wherein the set of primers comprises primers having random nucleotide sequences.

40. A method of amplifying a target nucleic acid sequence, the method comprising, bringing into contact a set of primers, DNA polymerase, and a target sample, and incubating the target sample under conditions that promote replication of the target sequence, wherein all of the primers in the set of primers are complementary to the same strand in the target sequence, wherein the set of primers has 3 or more primers, wherein replication of the target sequence results in replicated strands, wherein during replication at least one of the replicated strands is displaced from the target sequence by strand displacement replication of another replicated strand.

41. A method of amplifying a target nucleic acid sequence, the method comprising, bringing into contact a set of primers, DNA polymerase, and a target sample, and incubating the target sample under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity, and wherein the set of primers comprises primers having random nucleotide sequences, wherein each primer comprises a constant portion and a random portion, wherein the constant portion of each primer has the same nucleotide sequence and the random portion of each primer has a random nucleotide sequence.

42. A method of amplifying a target nucleic acid sequence, the method comprising, bringing into contact a set of primers, DNA polymerase, and a target sample, and incubating the target sample under conditions that promote replication of the target sequence, wherein replication of the target sequence results in replicated strands, wherein during replication at least one of the replicated strands is displaced from the target sequence by strand displacement replication of another replicated strand, wherein the conditions that promote replication of the target sequence do not involve thermal cycling, and wherein the target sequence is concatenated DNA.

* * * * *